United States Patent [19]

Kuhls

[11] 4,282,162

[45] Aug. 4, 1981

[54] RECOVERY OF FLUORINATED EMULSIFYING ACIDS FROM BASIC ANION EXCHANGERS

[75] Inventor: Jürgen Kuhls, Burghausen, Fed. Rep. of Germany

[73] Assignee: Hoechst Aktiengesellschaft, Fed. Rep. of Germany

[21] Appl. No.: 115,803

[22] Filed: Jan. 28, 1980

[30] Foreign Application Priority Data

Feb. 2, 1979 [DE] Fed. Rep. of Germany ....... 2903981

[51] Int. Cl.$^3$ .......................... C07C 51/42; C08F 1/88
[52] U.S. Cl. ................................ 260/408; 260/428.5; 260/513 F; 562/605
[58] Field of Search ................. 260/408, 428.5, 513 F; 562/605

[56] References Cited

U.S. PATENT DOCUMENTS

| | | | |
|---|---|---|---|
| 2,863,889 | 12/1958 | Marks | 260/408 |
| 3,882,153 | 5/1975 | Seki et al. | 260/408 |
| 4,005,137 | 1/1977 | Ruldolph et al. | 562/605 |

FOREIGN PATENT DOCUMENTS 2754457 6/1979 Fed. Rep. of Germany ....... 260/513 F

*Primary Examiner*—John F. Niebling
*Attorney, Agent, or Firm*—Connolly and Hutz

[57] ABSTRACT

To elute fluorinated emulsifying acids, especially perfluoro-carboxylic acids, from basic anion exchangers a mixture of dilute mineral acid and polar organic solvents is used. The solvent should be miscible with water preferably to an extent of at least 40%. By this process the required amount of eluent and the time of elution can be reduced while simultaneously the amount of recovered emulsifying acid can be improved. The process is especially suitable for the recovery of fluorinated emulsifiers in the coagulation or concentration of fluoropolymer latices.

5 Claims, No Drawings

RECOVERY OF FLUORINATED EMULSIFYING ACIDS FROM BASIC ANION EXCHANGERS

This invention relates to a process for eluting fluorinated emulsifying acids adsorbed on basic anion exchangers.

In the polymerization of fluorinated monomers in aqueous dispersion generally only fluorinated emulsifiers can be successfully used because of the required telongenic inactivity. Emulsifiers of this type are, above all, the salts, preferably the alkali metal or ammonium salts, of perfluorinated or partially fluorinated alkanoic acids or of perfluorinated or partially fluorinated alkane-sulfonic acids. The manufacture of fluorinated emulsifiers of this type be electrofluorination or telomerization of fluorinated monomers involves high costs and, therefore, the fluorinated emulsifiers are rather expensive. To save costs it is thus very important to recover the proportion of fluorinated emulsifier dissolved in the aqueous phase after the coagulation of the polymer from the dispersion or in aqueous polymer dispersions to be concentrated. This can be done especially successfully by adsorption with the aid of ion exchangers with subsequent elution.

U.S. Pat. No. 3,882,153 describes a process for the adsorption with the aid of weakly basic anion exchangers of perfluorocarboxylic acids or the salts thereof contained in the aqueous phase of coagulated polytetrafluoroethylene dispersions. In this patent it is disclosed to use a dilute aqueous ammonia solution for the subsequent elution of the adsorbed fluorinated emulsifier.

The aforesaid process has two essential drawbacks. Firstly, relatively large amounts of dilute NH$_4$OH solution are required for complete elution and secondly too long a period of time is necessary to attain this objective. Moreover, as soon as the elution is terminated the ion exchanger has to be converted, in a following regeneration process using dilute mineral acid, into the anion form, preferably the chloride form, especially suitable for each following adsorption of the fluorinated emulsifiers generally present in salt form.

It is, therefore, the objective of the present invention considerably to reduce the amount of eluting agent necessary for the elution and, hence, the required time and simultaneously to regenerate the anion exchanger so that it can be used again for adsorbing the fluorinated emulsifying acids.

This problem is solved, in accordance with the present invention, by using a mixture of a dilute mineral acid and an organic solvent for the elution of the adsorbed fluorinated emulsifying acids from the anion exchangers.

The term fluorinated emulsifying acids in this context is intended to include, above all, perfluorinated alkanoic acids of the formula $CF_3(CF_2)_nCOOH$ in which n is a number from 3 to 10, preferably perfluorooctanoic acid, which give the best results when eluted by the process of the invention. The term likewise includes partially fluorinated alkanoic acids of the formula $XCF_2(CF_2)_nCOOH$ in which X is hydrogen or chlorine and n is a number from 3 to 10, perfluorinated or partially fluorinated alkane-sulfonic acids of the formula $XCF_2(CF_2)_nSO_3H$ in which X is hydrogen and preferably fluorine and n is a number from 3 to 10 and perfluoro-[($\beta$-propoxy)-propionic acid].

Fluorinated emulsifying acids of these types can also be eluted by the process of the invention. It is likewise possible to adsorb and elute mixtures of the aforesaid emulsifying acids, especially those containing a predominant proportion of perfluorooctanoic acid.

For adsorption the aforesaid fluorinated emulsifying acids are contacted with the anion exchanger in the form of the solutions to be worked up usually containing same in the form of their salts, preferably their alkali metal and ammonium salts. The solutions to be worked up may additionally contain fluoride ions and other dispersing agents, for example non-ionic oxalkylates of alcohols or phenols, without the recovery of the fluorinated emulsifying acids according to the invention being affected.

Suitable mineral acids are all those the anions of which confer a salt form upon the anion exchanger (anion form) which is appropriate to the further adsorption of fluorinated emulsifying acids. Under the conditions of elution their oxidation strength should be so low that the anion exchanger will not be damaged oxidatively. Mineral acids to be used are, for example ortho-, meta-, and diphosphoric acid, nitric acid and preferably hydrochloric acid and sulfuric acid.

As organic solvent all those can be used which neither impede, in the acid-aqueous medium used, the function of the anion exchanger used, for example by swelling or dissolution, nor enter into an undesired reaction with the mineral acid used. Solvents of this type are polar organic solvents such as chlorohydrocarbons, aliphatic or aromatic ethers and carboxylic acid esters. There are preferred solvents that are substantially miscible with water that means miscible to at least 40% by volume when mixing equal volumes, or solvents that are completely miscible with water. Solvents of this type are especially aliphatic alcohols having from 1 to 4 carbon atoms, preferably methanol and ethanol, cyclic ethers such as tetrahydrofurane and dioxane, short chain, dialkyl-substituted amides such as dimethyl formamide or dimethyl acetamide as well as mono- and dimethyl ethers and mono- and diethyl ethers of ethylene glycol or of the corresponding polyglycols having a chain length up to that of decaethylene glycol. It is likewise possible to use mixtures of the aforesaid solvents.

A mixture is prepared from the mineral acid and the organic solvent to be used the acid strength of which, calculated on the total mixture, is adjusted in the range of from 0.5 to 10 N, preferably 0.5 to 2 N. In said mixture the proportion of mineral acid (including the water portion) to solvent ranges from 1:0.25 to 1:20, preferably 1:3 to 1:10 parts by volume.

For the adsorption of the fluorinated emulsifying acids to be carried out prior to the elution weakly basic anion exchangers are preferred which contain primary, secondary and preferably tertiary amino groups in the form of the ammonium salts (for example the types MP 62 of Messrs. Bayer AG, Leverkusen, and IRA 68 of Messrs. Serva, Heidelberg, Federal Republic of Germany). Strongly basic anion exchangers generally containing quaternary ammonium groups can also be used (for example the type M 600 of Messrs. Bayer AG, Leverkusen). In general, the strongly basic anion exchangers exhibit a sufficient adsorption power for the emulsifying acids or their salts in the OH form only and therefore, after the elution, they have to be converted again into the OH form by the addition of a strong base, for example sodium hydroxide solution.

For a quantitative elution of the adsorbed emulsifying acids 50 to 500 and preferably 100 to 225 parts by volume, calculated on 100 parts of anion exchanger matrix, of the mixture of mineral acid and organic solvent is required.

When the elution is terminated the eluate generally separates into two layers of which the lower layer having the higher specific gravity contains practically the entire amount of fluorinated emulsifying acid. The lower layer is neutralized with dilute, usually 2 N sodium hydroxide solution and the emulsifying acid is precipitated in compact form and easy to separate by adding the neutralized phase while stirring to dilute hydrochloric acid.

The temperature at which the elution according to the invention is carried out is not critical. It is expediently carried out at room temperature, that is to say a temperature range of from 15° to 25° C. In some cases a temperature increase may prove advantageous.

As compared to the known elution with dilute, aqueous ammonia solution, the process of the invention offers some substantial advantages. It can be seen from Table I below that the required amount of eluting agent can be drastically reduced so that the time necessary for the regeneration of the anion exchanger can be shortened. At the same time the yield of recovered fluorinated emulsifying acid is increased. In many cases it is almost quantitative. Owing to the fact that in the process of the invention dilute mineral acids are used in admixture with organic solvents a weakly basic anion exchanger is converted into its original salt form during the elution. Consequently, the regeneration step of such a weakly basic anion exchanger into the salt form by means of a dilute mineral acid after each elution can be dispensed with.

The separation and recovery of fluorinated emulsifying acids is of importance, above all, with aqueous solutions obtained in precipitation and coagulation processes during the processing of emulsion polymers of fluorinated monomers, that is to say, in the first place, of homo- and copolymers of tetrafluoroethylene, vinylidene fluoride, vinyl fluoride and trifluorochloroethylene, or aqueous emulsions resulting from the manufacture of fluorocarbon telomer waxes. Fluorinated emulsifying acids can also be separated and recovered according to the invention from aqueous solutions obtained in the concentration of fluoropolymer latices, especially processes with phase separations. Residues of catalysts, inorganic salts or non-ionic dispersing agents, for example alkoxylated alkylphenols or alkoxylated aliphatic alcohols or alkylene oxide block polymers possibly contained in the aqueous solutions interfere neither in the adsorption nor in the elution step.

In the following Table I an elution of perfluorooctanoic acid with ammonia is compared with the elution carried out with a mixture of dilute mineral acid with organic solvent.

TABLE I

| Process step | Example 1 of U.S. Pat. No. 3,882,153 | Example 4 of invention (cf. Table II below) |
|---|---|---|
| (1) elution | | |
| eluent | 1N NH$_4$OH | conc. HCl/ethanol |
| amount in cc | 800 | 50/250 |
| time in minutes | 60 | 10 |
| (2) regeneration of anion exchanger | treatment with 800 cc of 1N HCl | not required |

In both cases a weakly basic anion exchanger (MP 62 of Messrs. Bayer, Leverkusen) in the chloride form, obtained by a treatment with dilute hydrochloric acid, is used for the adsorption of perfluorooctanoic acid. Dimensions and amount of exchanger are specified in the following procedure of the examples.

The following examples illustrate the invention without limiting it thereto.

EXAMPLES 1–16

(a) Adsorption

Unless otherwise stated, 200 cc of weakly basic anion exchanger MP 62 (manufacturer Bayer AG, Leverkusen) are introduced into a cylindrical glass column provided with glass frit and having a length of 64 cm and a diameter of 20 mm and, by passing through 800 cc of 1 N mineral acid, the exchanger is transformed into the salt form indicated in column 2 of Table II. Next, 2 liters of an aqueous solution containing 70 g of perfluorooctanoic acid and adjusted to pH 4 by dilute ammonia, which solution resulted from the coagulation of polytetrafluoroethylene, are passed over the exchanger within one hour. The amounts of emulsifying acid adsorbed on the column is indicated in column 3 of Table II.

(b) Elution

The composition and amount of eluting mixture and the period of time required to reach the indicated degree of elution of perfluorooctanoic acid are indicated in column 4 of Table II. In general, the eluate consists of two layers and in all cases the lower layer having a high specific gravity contains almost the entire amount of perfluorooctanoic acid. The lower layer is separated from the upper layer, neutralized with 2 N NaOH and the emulsifying acid is precipitated by adding the separated layer while stirring to 1,000 cc of 2 N hydrochloric acid. The perfluorooctanoic acid crystals are then separated by filtration, washed with dilute hydrochloric acid and dried.

TABLE II

Adsorption and elution of perfluorooctanoic acid from basic anion exchangers

| Ex. No. | salt form of anion exchanger | adsorption of perfluorooctanoic acid (g) | elution of perfluorooctanoic acid with | | | | time required (min) | eluted amount (g) | % of adsorbed amount |
|---|---|---|---|---|---|---|---|---|---|
| | | | organic solvent (cc) | | mineral acid (cc) | | | | |
| 1 | Cl$^-$ | 67 | methanol | (250) | HCl conc. | (50) | 10 | 65 | 97 |
| 2 | OH$^-$ | 10 | methanol | (250) | HCl conc. | (50) | 12 | 8 | 80 |
| 3 | SO$_4^{2-}$ | 60 | methanol | (250) | HCl conc. | (50) | 11 | 45 | 75 |
| 4 | Cl$^-$ | 62 | ethanol | (250) | HCl conc. | (50) | 10 | 60 | 97 |
| 5 | Cl$^-$ | 68 | n-propanol | (250) | HCl conc. | (50) | 12 | 67 | 99 |
| 6 | Cl$^-$ | 60 | dioxane | (250) | HCl conc. | (50) | 11 | 60 | 100 |
| 7 | Cl$^-$ | 62 | diethyl ether | (250) | HCl conc. | (50) | 13 | 40 | 65 |
| 8 | Cl$^-$ | 64 | dimethylformamide | (250) | HCl conc. | (50) | 10 | 61 | 95 |
| 9 | Cl$^-$ | 64 | methylene | (250) | HCl conc. | (50) | 14 | 32 | 50 |

TABLE II-continued

Adsorption and elution of perfluorooctanoic acid from basic anion exchangers

| Ex. No. | salt form of anion exchanger | adsorption of perfluoro-octanoic acid (g) | elution of perfluorooctanoic acid with | | | | time required (min) | eluted amount (g) | % of adsorbed amount |
|---|---|---|---|---|---|---|---|---|---|
| | | | organic solvent (cc) | | mineral acid (cc) | | | | |
| 10 | $Cl^-$ | 60 | chloride methanol | (250) | $H_2SO_4$ conc. | (25) | 10 | 50 | 83 |
| 11 | $OH^{-2}$ | 52 | methanol | (250) | HCl conc. | (50) | 12 | 38 | 73 |
| 12 | $OH^{-2}$ | 50 | methanol | (250) | $H_2SO_4$ conc. | (25) | 12 | 35 | 70 |
| 13 | $Cl^-$ | 60 | methanol | (500) | HCl conc. | (100) | 12 | 50 | 83 |
| 14 | $OH^{-3}$ | 68 | methanol | (250) | HCl conc. | (50) | 13 | 50 | 83 |
| 15 | $Cl^-$ | 59[4] | ethanol | (250) | HCl conc. | (50) | 15 | 39 | 66 |
| 16 | $Cl^-$ | 67 | ethanol | (250) | $H_3PO_4$ + $H_2O$ | (50 g) (150 cc) | 20 | 32 | 48 |

[1] concentrated HCl 37% strength by weight, concentrated $H_2SO_4$ 98% strength by weight $H_3PO_4$ 85% by weight
[2] strongly basic anion exchanger M 600 (Bayer AG, Leverkusen)
[3] weakly basic anion exchanger IRA 69, amberlite (Serva, Heidelberg)
[4] instead of perfluorooctanoic acid, the solution contains 70 g of perfluoro-n-octane-sulfonic acid n-$C_8F_{17}SO_3H$ in 2 liters of prior to its passage through the ion exchanger.

What is claimed is:

1. Process for eluting fluorinated emulsifying acids adsorbed on basic anion exchangers, which comprises eluting the adsorbed fluorinated emulsifying acid from the anion exchanger with a mixture of a dilute mineral acid and an organic solvent.

2. The process of claim 1, wherein 0.5 to 10 N mineral acid is used in admixture with an organic solvent and the proportion of aqueous mineral acid to organic solvent is in the range of from 1:0.25 to 1:20.

3. The process of claims 1 and 2, wherein the fluorinated emulsifying acid to be eluted is a perfluorocarboxylic acid of the formula $CF_3(CF_2)_n COOH$ in which n is a number from 3 to 10.

4. The process of claims 1 to 3, wherein hydrochloric acid is used as dilute mineral acid.

5. The process of claims 1 to 4, wherein the organic solvent is miscible with water to an extent of at least 40% by volume.

* * * * *